United States Patent [19]

Argyle et al.

[11] Patent Number: 5,181,536
[45] Date of Patent: Jan. 26, 1993

[54] COOLANT CORROSIVENESS INDICATOR

[75] Inventors: Charles S. Argyle, Willowdale; Brian E. Cheadle, Bramalea, both of Canada; Steven L. M. Bokor, Rochester Hills, Mich.

[73] Assignee: Long Manufacturing Limited, Oakville, Canada

[21] Appl. No.: 821,631

[22] Filed: Jan. 16, 1992

Related U.S. Application Data

[62] Division of Ser. No. 610,804, Nov. 8, 1990, Pat. No. 5,127,433.

[30] Foreign Application Priority Data

Apr. 19, 1990 [CA] Canada ................. 2014982

[51] Int. Cl.⁵ ............. F16K 37/00; F28F 19/00; G01D 21/00
[52] U.S. Cl. .................... 137/559; 165/11.1; 116/206; 116/215; 73/61.61; 73/86; 73/440
[58] Field of Search .............. 137/559; 165/11.1; 62/125, 129; 116/206, 215, DIG. 1, 2; 73/86, 440, 445, 448, 61.61, 61.41

[56] References Cited

U.S. PATENT DOCUMENTS

| | | | |
|---|---|---|---|
| 2,067,440 | 1/1937 | Finney | 165/11.1 |
| 2,757,632 | 8/1956 | Wittlin | 62/129 X |
| 3,084,658 | 4/1963 | Schell | 116/206 |
| 3,085,424 | 4/1963 | Berg | 62/125 X |
| 3,122,011 | 2/1964 | Pritchett | 62/129 X |
| 3,225,555 | 12/1965 | Chatlos | 62/125 X |
| 3,490,271 | 1/1970 | Hays | 73/86 |
| 3,585,963 | 6/1971 | Hiszpanski | 116/206 |
| 3,621,810 | 11/1971 | Zuck | 73/86 X |
| 3,734,168 | 5/1973 | Degroote | 165/11.1 |
| 3,874,323 | 4/1975 | Röttig | 62/125 X |
| 3,976,121 | 8/1976 | Johnson | 165/11.1 |
| 4,273,744 | 6/1981 | Krueger | 422/265 |
| 4,306,127 | 12/1981 | Payne | 200/61.04 |
| 4,333,516 | 6/1982 | Krueger | 165/1 |
| 4,338,959 | 7/1982 | Krueger | 165/11.1 X |
| 4,628,252 | 12/1986 | Terhune | 73/86 X |
| 4,736,628 | 8/1988 | Lin | 73/440 |

FOREIGN PATENT DOCUMENTS 1076894 5/1980 Canada .
250567 7/1926 Switzerland .

Primary Examiner—John Rivell
Attorney, Agent, or Firm—Baker & Daniels

[57] ABSTRACT

A fluid sensor for heat exchanger system includes a supporting device such as a tubular hose fitting for mounting the sensor in the system so that heat exchanging fluid circulated in the system comes into contact with the sensor. A window or sight glass is mounted in the supporting device along with corrodible separating means interposed between the sight glass and the heat exchanging fluid. A visual indicator such as a movable flap or a coloured ball can be viewed through the sight glass when the separating means is ruptured or broken by corrosion. The viewing of the indicator provides an indication that the heat exchanging fluid has reached a certain corrosive state and requires replacement or treatment. In a preferred embodiment, the separating means is a metal diaphragm spaced from the sight glass. The diaphragm can be made of one corrodible metal while a ring in which the diaphragm is mounted can be made from a different nobler metal so that the diaphragm and ring form an anode and a cathode of a galvanic couple.

8 Claims, 8 Drawing Sheets

COOLANT CORROSIVENESS INDICATOR

This is a division of application Ser. No. 07/610,804 filed Nov. 8, 1990 now U.S. Pat. No. 5,127,433.

BACKGROUND OF THE INVENTION

This invention relates to fluid condition sensors or indicators intended for use in a heat exchanger system such as a radiator or air conditioning system.

A well known engine coolant for an automotive vehicle contains a solution of ethylene glycol and a small percentage of diethylene glycol diluted with water to make an approximately 50—50 mixture or lower depending on the desired freezing point for the solution. Generally, manufacturers or distributors of ethylene glycol add one or more corrosion inhibitors to the solution to protect the metal components of the engine cooling system, particularly the radiator. These inhibitors are usually a mixture of one or more inorganic salts such as phosphates, borates, nitrates, nitrites, silicates or arsenates and organic compound. The solution is usually buffered to a pH of 8 to 10 to reduce iron corrosion and to neutralize any glycolic acid.

It is very important that the coolant mixture in an engine cooling system contain 50 to 55% of properly inhibited ethylene glycol to prevent corrosion of conventional copper-brass radiators. Also, aluminum radiators have now come into use and such radiators are even more susceptible to corrosion. The problem of corrosion can be caused simply by the addition of ordinary water to the cooling system by a driver when he is low in coolant. For example, a reduction of the coolant mixture to 33% ethylene glycol and 67% water will increase metal corrosion significantly, especially in higher temperature coolant systems.

U.S. Pat. No. 4,338,959 issued Jul. 13, 1982 to Borg-Warner Corporation teaches a device for the automatic addition of corrosion inhibitor to a cooling system including an electronic control circuit having a probe or sensor which indicates corrosion rates in an engine cooling system and provides a signal to a solenoid activating a control valve which automatically adds a controlled amount of corrosion inhibitors solution to the cooling system. However, this known system has certain disadvantages, one of which is the amount of room required to install the system in a vehicle. For example, the system requires a container capable of holding an adequate reserve charge of corrosion inhibitor. Also, there is a significant expense involved in providing this system in a vehicle because of the cost of the corrosion inhibitor and other required components.

U.S. Pat. No. 4,306,127 issued Dec. 15, 1981 to Robertshaw Controls Company describes a corrosion sensor having a housing containing an electric switch mechanism. A switch actuator is held in one operating position by a corrosion sensing member formed from a disk of aluminum foil that spans one end of the housing. The actuator moves to another switch operating position when the aluminum foil ruptures through the corrosion thereof caused by being exposed to a corrosive area. A flexible diaphragm is carried by the housing in stacked engaging relation with the aluminum disk and acts to prevent corrosive material from entering the housing when the aluminum disk ruptures.

U.S. Pat. No. 4,736,628 issued Apr. 12, 1988 to V. S. Lynn describes a testing device for a car battery or radiator, which device includes a transparent box-like housing forming a partitioned chamber. There are a plurality of channels in which a plurality of balls having various densities are contained. The fluid to be tested enters the housing through a tubular element at the top. The number of floating balls in the housing indicates the specific gravity of the fluid and the freezing and boiling point thereof.

Test results reported in a paper co-authorized by one of the present inventions (Brian Cheadle) confirm that relatively high degrees of coolant depletion are required to initiate corrosion damage in aluminum cylinder head material compared to corrosion of a corrodible diaphragm. This paper entitled "Controlled Release of Inhibitors for Extended Protection of Aluminum Engine Cooling Systems" was published by the Society of Automotive Engineers as Paper 820287 in 1983.

SUMMARY OF THE INVENTION

The present invention provides a rather inexpensive fluid condition sensor which will provide a visual indication to the user that the heat exchanging fluid has reached a certain corrosive state. Generally, the device employs a sight glass or window through which an indicator of the corrosive state can be seen or through which the heat exchanging fluid can be seen. In the second version, the presence of the fluid behind the sight glass indicates a corrosive state. The sensor employs a corrodible separating mechanism such as a diaphragm or a coating on the sight glass which is normally interposed between the sight glass and the heat exchanging fluid and which is in contact with the heat exchanging fluid during use of a sensor.

According to one aspect of the invention, a fluid condition sensor for a heat exchanger system includes support means for mounting the sensor in a system in such a manner that heat exchanging fluid circulated in a system comes into contact with the sensor and a sight glass mounted in the support means. There is a corrodible separating means interposed between a sight glass and the heat exchanging fluid and located so that the heat exchanging fluid contacts the separating means during use of the sensor. A visual indicator can be viewed through the sight glass when the separating means is removed, ruptured or broken by corrosion. The viewing of this indicator provides an indication that the heat exchanging fluid has reached a certain corrosive state.

According to another aspect of the invention, a corrosion sensor for a heat exchanger system includes support means for mounting the sensor in a system to enable the sensor to contact heat exchange fluid flowing through the system and a corrodible diaphragm mounted in the support means where the fluid can contact one side of the diaphragm during use of the sensor. There is also a sight glass mounted in the support means on the other side of the diaphragm, a normally empty chamber being arranged between the diaphragm and the sight glass. The diaphragm is selected and constructed so as to corrode and rupture before the heat exchange fluid becomes so corrosive that it can cause significant damage to the heat exchange system. A rupture of the diaphragm causes the fluid to flow into the chamber and thereby indicates a need to change or treat the heat exchange fluid.

In one preferred embodiment of this sensor, the support means is a tubular hose fitting having an inlet and an outlet for the heat exchanging fluid and an opening in one side thereof in which the diaphragm and the sight glass are mounted. This preferred embodiment is suitable for installation as either original equipment in a vehicle cooling system or for subsequent installation after sale.

According to a further aspect of the invention, a corrosion sensor for a heat exchanger system includes supporting means for mounting the sensor in the system to enable the sensor to contact heat exchanging fluid flowing through the system and a visual indicator mounted in the support means and movable from a first position indicating that the heat exchanging fluid is in a non-corrosive state to a second position indicating that the fluid has become corrosive to at least a limited degree. There is also a corrodible release mechanism for holding the indicator in the first position and located so as to be immersed in the heat exchanging fluid during use of the sensor. A sight glass is mounted in or on the support means and the indicator is visible through the sight glass. The release mechanism corrodes and breaks when the fluid becomes corrosive to at least a limited degree, thereby releasing the indicator so that it moves to the second position.

In a preferred version of this sensor, the visual indicator is a pivotable flap having different colours on opposite sides of the flap and the release mechanism is a straight metal wire or metal spring, one end of which is connected to the flap and the other end of which is connected to the support means.

BRIEF DESCRIPTION OF THE DRAWINGS

Further features and advantages of a present fluid condition sensor will become apparent from the following detailed description taken in conjunction with the accompanying drawings which illustrate various preferred embodiments, in which.

DETAILED DESCRIPTION OF THE PREFERRED EMBODIMENTS

Figure 1:
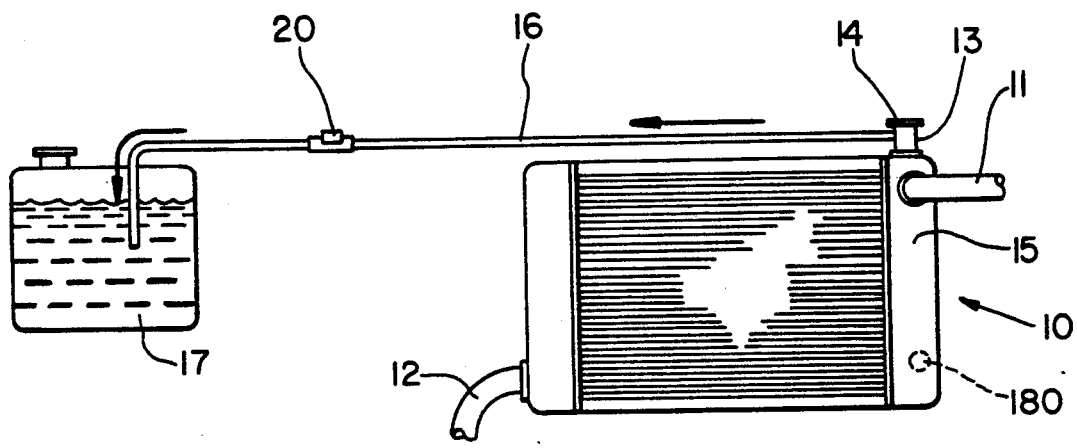
FIG. 1 is schematic view of a radiator and overflow reservoir for a vehicle cooling system employing the present invention.

FIG. 1 illustrates a portion of a cooling system for an automotive vehicle including a radiator 10 (which is a form of heat exchanger) having an inlet 11 for hot coolant from the vehicle engine jacket and an outlet 12 leading to a coolant pump for the engine. The top of the radiator is a pressure relief vent cap 14 on a filler neck 13. This neck is located at the top of an inlet tank 15 for the radiator. An overflow line 16 leads from the vent cap to an overflow reservoir 17 for the coolant.

Interposed in the overflow conduit 16 is a fluid condition sensor 20, the details of which are explained hereinafter. This sensor 20 is provided to enable the user of the vehicle or a mechanic responsible for the maintenance of same a visual indication through a sight glass or window of the sensor as to whether the heat exchanging fluid in the system has reached a certain corrosive state. An indication can be provided by the viewing of a flap or ball through the window, the flap or ball displaying a colour indicating the need for a change of the heat exchanging fluid or, alternatively, the need for the addition of corrosion inhibitors. The indication of a corrosive state can also be provided simply by the presence of heat exchanging fluid on the inside surface of the window or sight glass where it can be clearly seen.

In a preferred version of the invention, the sensor is constructed so that the visual indicator will be triggered or present before the heat exchange fluid becomes so corrosive that it can cause significant damage to the radiator or heat exchange system. Thus, the user of the vehicle or the mechanic is advised by the indicator to change or treat the heat exchange fluid before considerable damage to the radiator or other major components of the system is caused.

Figure 2:
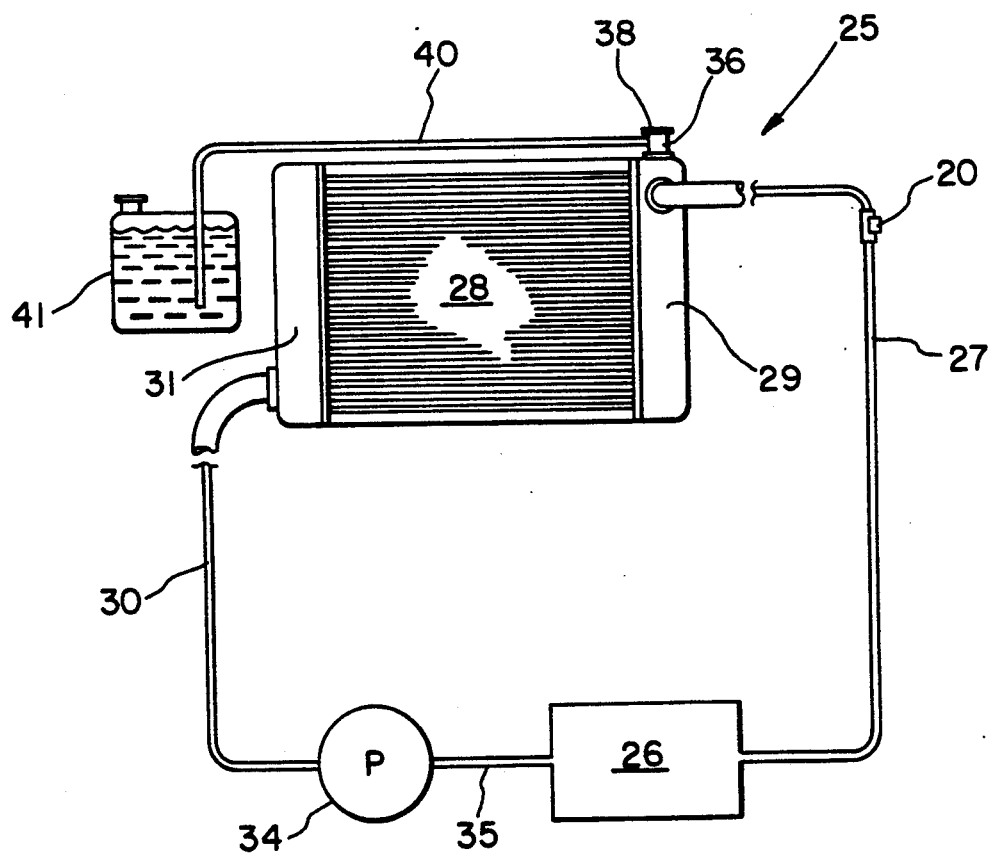
FIG. 2 is a schematic view of a vehicle cooling system wherein the present invention is installed at an alternate location in the system.

FIG. 2 illustrates an alternate arrangement for installing a fluid condition sensor constructed in accordance with the invention in a vehicle cooling system indicated generally at 25. This system includes an engine 26 or other heat source having a cooling jacket, a hot fluid conduit 27 from the engine to the inlet tank 29 of a radiator 28, and a cooled fluid conduit 30 from the outlet tank 31 leading to a fluid pump 34 operated by the engine to pump the coolant through a conduit 35 to the cooling jacket. A filler neck 36 on inlet tank 39 has a pressure relief cap 38 and an overflow conduit 40 leads from the neck to an overflow reservoir 41. A corrosion sensor 20 constructed in accordance with the invention is positioned in the conduit 27 and is in the form of a tubular pipe fitting that can be readily attached in a break provided in the conduit 27.

Figure 3:
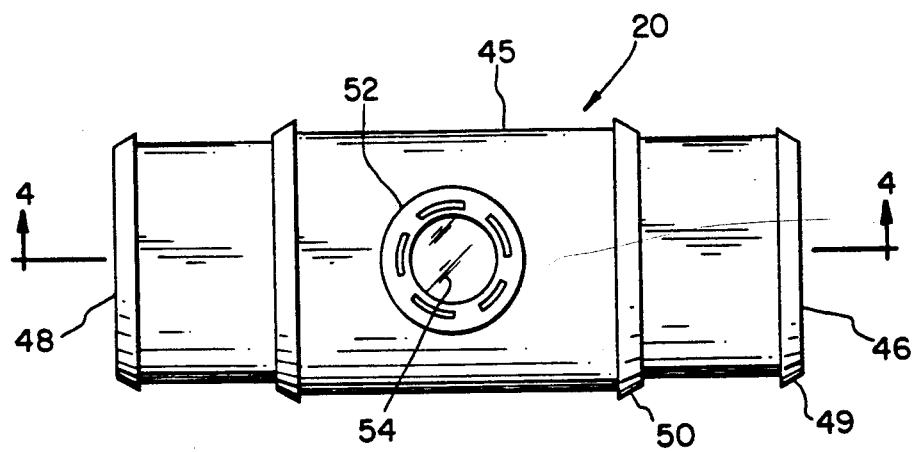
FIG. 3 is a top view of a first version of the invention arranged in a tubular hose fitting.
Figure 4:
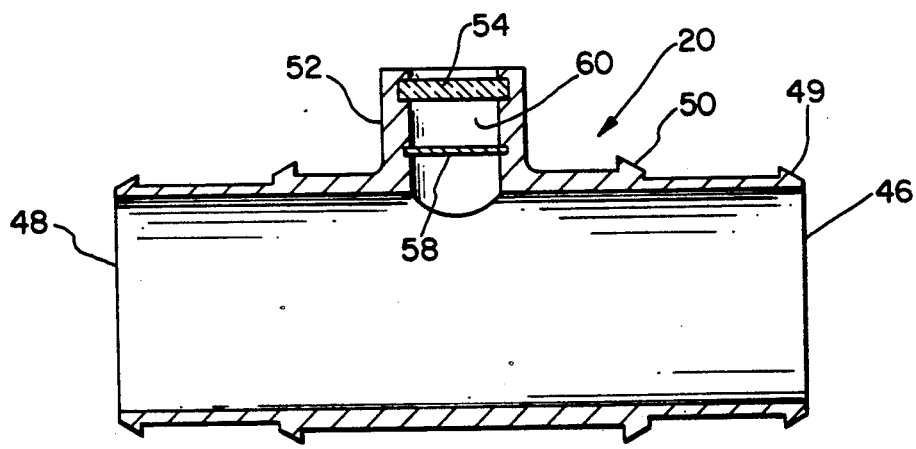
FIG. 4 is an axial cross-sectional view taken along the line IV—IV of FIG. 3.

A first version of a fluid condition sensor 20 constructed in accordance with the invention is illustrated in detail in FIGS. 3 and 4. The sensor includes support means 45 for mounting the sensor in the heat exchanger or radiator system in such a manner that heat exchanging fluid circulated in the system comes into contact with the sensor. The support means shown in FIGS. 3 and 4 is in the form of a tubular hose fitting having an inlet 46 at one end and an outlet 48 for the heat exchanging fluid at the other end. Annular ridges 49 and 50 can be provided on the exterior of a fitting to assist in the attachment of a hose. The fitting which is in the form of a T has a cylindrical extension 52 on one side located midway along the length of the fitting. Mounted in this extension is a sight glass means or window 54 which is transparent or translucent so that one looking through the sight glass can view material, shapes or colours therethrough. The term "sight glass means" as used herein includes not only a small window or viewing piece made of glass but also other suitable transparent or translucent material such as clear plastics that are able to withstand the temperatures at which the heat exchanger or radiator operates. The sight glass can be mounted securely in place by known mechanical means such as crimping, clamping or screwing. Alternatively, it can secured by a suitable adhesive.

The sensor also has corrodible separating means 58 interposed between the sight glass 54 and the heat exchanging fluid passing through the fitting. In the embodiment of FIGS. 3 and 4, the separating means comprises a metal diaphragm mounted in the extension 52 and spaced from the sight glass so that there is a normally empty chamber 60 arranged between the diaphragm and the sight glass. A variety of corrodible materials can be used for the diaphragm including aluminum and magnesium alloys.

A visual indication of the corrosive state of the heat exchanging fluid is provided by the sensor 20 when the separating means 58 is ruptured or broken by corrosion caused by the corrosive state of the heat exchanging fluid. It will be appreciated that when the diaphragm does rupture, the heat exchanging fluid will enter the chamber 60 where it can be viewed through the sight glass. The presence of the heat exchanging fluid below or next to the sight glass indicates to the user of a vehicle that the heat exchanging fluid or coolant must either be replaced or treated with inhibitors so that the corrosiveness of the fluid is reduced to safe limits. If desired, a small pellet or wafer of dye or dye containing material can be inserted in the chamber 60. This will cause the colour of the fluid entering the chamber to change to a clearly visible colour (for example red). In the alternative, the wafer itself can be made to change colour in the presence of the fluid in order to indicate the onset of corrosive conditions.

As discussed in more detail hereinafter, tests have shown that selected or candidate corrodible materials perforate much faster than standard radiator materials in the same corrosive environment. Thus the ability for a corrodible diaphragm to be broken or perforated at an early stage to provide the required indication of a corrosive condition prior to damage to the cooling system is demonstrated in test results. In addition, these tests indicate that these corrodible materials used for the diaphragm do not corrode or perforate in a fully inhibited coolant. Therefore a corrosive condition should not be indicated prematurely by the present sensors as described herein.

The diaphragm can be secured in place in a pipe fitting in a variety of ways including known mechanical methods such as crimping, clamping, and screwing and including magneforming. Welding brazing or soldering are further possible methods of attachment. Adhesive bonding can be used but if galvanic contact is required, the adhesive must be conductive.

Figure 5:
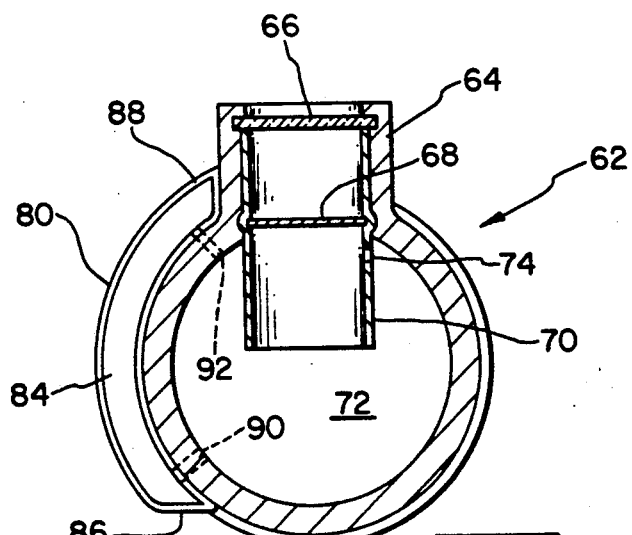
FIG. 5 is a transverse cross-sectional view taken along the line V—V of FIG. 6 of another embodiment of the invention, again arranged in a tubular hose fitting.
Figure 6:
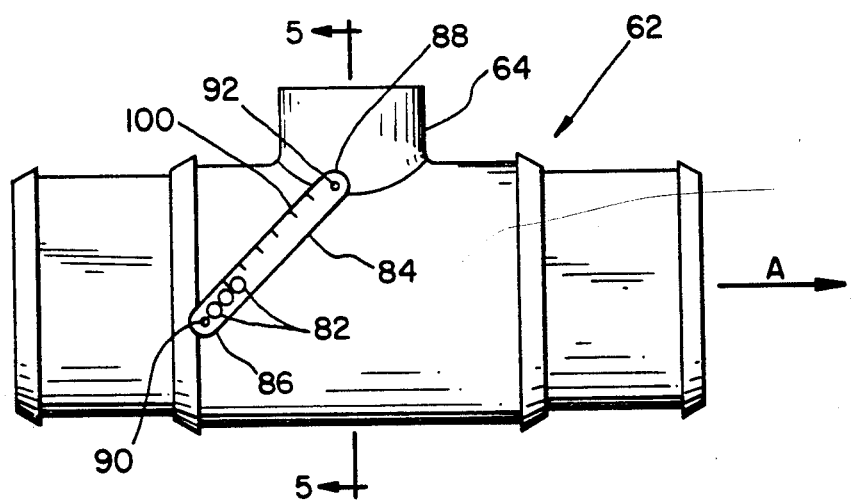
FIG. 6 is a side view of a tubular pipe fitting incorporating one version of the invention.

Turning now to the embodiment shown in FIGS. 5 and 6 of the drawings, this sensor 62 is also in the form of a tubular pipe fitting with a cylindrical extension 64. As in the embodiment of FIG. 4, there is a sight glass or window 66 mounted near the outer end of the extension and spaced below this window is a corrodible metal diaphragm 68. However, in this embodiment the diaphragm is mounted in a metal tubular member 70, the top portion of which is located in the extension 64 and a bottom portion of which extends into a main passageway 72 of the tubular fitting. In order to cause the diaphragm 68 to corrode quickly when the heat exchanging fluid reaches a corrosive state, the diaphragm 68 and the member 70 are constructed and arranged to form a galvanic couple with the diaphragm being the anode and the tubular member 70 being the cathode. Both the anode and cathode are exposed to the coolant that is flowing through the passageway 72. The diaphragm 68 must be mounted so that it is in mechanical contact with the member 70. The diaphragm can be mounted by magneforming or mechanical assembly.

In order to prevent air from being trapped in the member 70 below the diaphragm 68, there is a hole 74 provided in the member 70 near the anode. The cathode 70 is made from a more noble metal than the metal forming the diaphragm 68. A preferred metal for the cathode is copper. Preferred materials for the anode are aluminum and magnesium alloys. The relevant surface areas of cathode and anode that are exposed to the coolant, as well as the selection of the anode and cathode materials are controlled by design factors to adjust the sensitivity of the couple to coolant corrosivity. The amount of the cathode exposed to the coolant should be relatively large as in the embodiment of FIGS. 5 and 6. A large cathode will provide a relatively large cathode: anode surface area ratio, thus ensuring an adequately large galvanic driving force so that there is a desirable sensitivity to coolant condition.

The embodiment of FIGS. 5 and 6 has a second visual indicator provided on the tubular fitting, the purpose of which is to indicate to the user or to the mechanic the density of the heat exchange fluid or coolant and the extent to which this fluid provides safe freeze point protection. The second visual indicator 80 is in the form of at least one coloured ball 82 and a transparent tube 84 for holding the ball or balls in heat exchanging fluid contained in the tube. The ball or balls are free to move to limited extent in the fluid, the amount of movement being limited by the internal dimensions of the tube 84. As shown this tube has a bottom end 86 and an upper end 88 located in the region of the extension 64. The flotation of one or more balls or the lack thereof indicates the density of the heat exchanging fluid or coolant which in turn indicates the extent to which the fluid provides safe freeze point protection.

In order to permit the circulation of heat exchanging fluid in the tube 80, two holes 90 and 92 extend between this tube and the interior of the tubular hose fitting and are positioned near opposite ends of the tube. Because the coolant is able to circulate in the tube 80, the fluid in the tube accurately and continuously represents the condition of the coolant in the system. Although the tube could extend perpendicularly to the central longitudinal axis of the fitting, preferably the tube 80 mounted on the exterior of the hose fitting extends at an acute angle to the central longitudinal axis as shown clearly in FIG. 6. By arranging the tube in this manner, the balls in the tube and the tube itself are visible from different angles and view points so that they can be seen without undue difficulty.

In the case of an indicator containing a number of balls 82, the balls will vary in density so as to provide a clear indication of the density of the fluid. For example, if only two balls are floating in the tube, that is it has risen to the top of the tube, and a third ball has sunk, this can indicate to the user that the fluid is slightly less dense than it would be if the fluid was in its ideal state (for example, that the percentage of water in the fluid exceeds 50%). If two balls have sunk in the tube, this indicates that the fluid is even less dense and perhaps is in need of further ethylene glycol solution. The sinking of all of the balls in the tube will indicate to the user that the heat exchange fluid is definitely too weak in strength and the percentage of water in the system must be reduced, possibly by the replacement of all of the heat exchanging fluid or coolant.

If only one coloured ball 82 is used in the tube 80, the amount by which the ball sinks in the tube 80 will provide the indication of fluid density. For this purpose, a scale or series of marks 100 can be provided on the tube. Numerical indicia (not shown) can also be provided on the tube to indicate to the user or mechanic the density of the fluid in the system or perhaps the safe freeze point provided by the fluid.

Preferably, the sensor of FIGS. 5 and 6 is installed in the upper hose of a radiator so that it will be readily visible when the hood of the car is raised. The engine of a car should be shut-off when one is going to obtain a reading of fluid density by viewing the tube 80 and the balls therein. Otherwise the flow of coolant through the system may cause the balls to move in the tube simply due to the fluid flow and not due to the density of the fluid. The sensor 62 should be installed in the system so that the fluid flow is in the direction indicated by the arrow A in FIG. 6. This will cause the fluid to flow into the hole 90 through the tube 80 and out through the hole 92. With the flow in this direction, the balls in the tube should not unduly interfere with the flow of fluid through the tube.

If a number of balls 82 are used in the sensor of FIGS. 5 and 6, the balls can have different colours to indicate densities. Also, if visible marks are required on the tube 80, these can be provided by printed sticker attached to the tube. Also the marks can be silk-screened on the surface of the tube.

Figure 7:
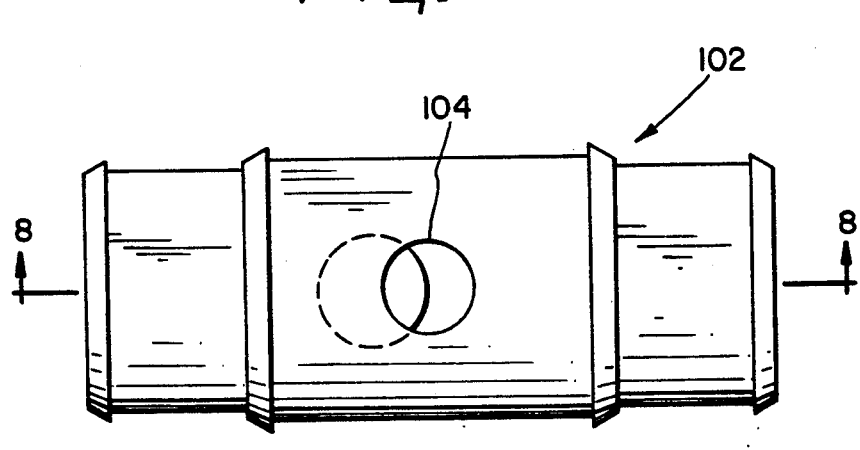
FIG. 7 is a side view of a further version of the invention arranged in a tubular pipe fitting.
Figure 8:
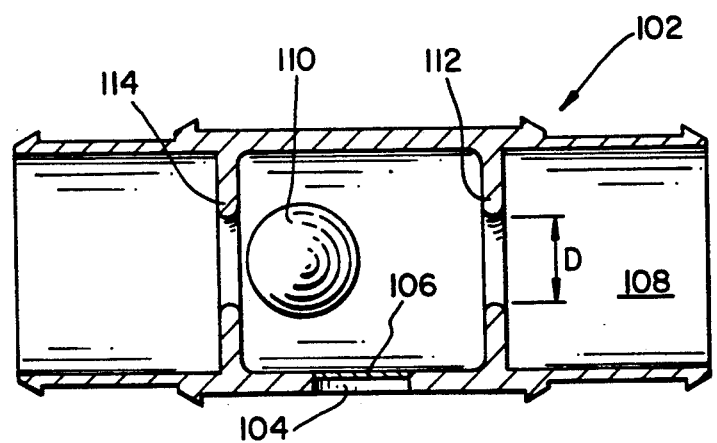
FIG. 8 is an axial cross-section of the version of FIG. 7 taken along the line VIII—VIII of FIG. 7.

Turning now to the embodiment illustrated by FIGS. 7 and 8, this sensor 102 is also in the form of a tubular fitting suitable for installation in the hose of a radiator system. The sensor 102 has a sight glass or window 104 mounted in the side thereof, preferably midway along the length of the fitting as shown. On the inside surface of this window is a corrodible opaque coating 106 covering the entire window. Preferably the coating is made of anodic material. This coating is not shown in FIG. 7 which shows the window 104 in its transparent from after the coating 106 has been corroded away. The coating 106 is of course located so that heat exchanging fluid passing through the passageway 108 of the fitting contacts the coating during use of the sensor. The coating can be totally adhered to the window or just at its periphery. A visual indicating means, which in this case is a coloured ball 110 can be viewed through the sight glass 104 when the opaque coating 106 is at least partially removed by corrosion. The greater degree of corrosion of course, the more the ball is visible. Instead of the ball 110, a coloured vane or a device like a thick fan blade could be used as the indicator. Also several small coloured balls can be used instead of a single ball provided their movement in the fitting is suitably restrained.

The sensor 102 includes means for restraining movement of the ball 110 in the sensor so that the ball will not flow out of the sensor and into the heat exchanger system. In the illustrated version the restraining means comprises two spaced-apart restrictions 112 and 114 arranged in the passageway 108, the ball 110 being located between these restrictions. The diameter D of a hole formed by each restriction is less than the diameter of the ball 110 so that the ball cannot pass by the restriction. The restriction should keep the ball in the vicinity of the sight glass so that the ball can be seen once the coating is corroded away. Preferably the ball is brightly coloured so that it can be seen even in poorer light conditions. If desired, two windows or sight glasses 104 can be provided in the sensor 102, these being located on opposite sides of the fitting.

Figure 9:
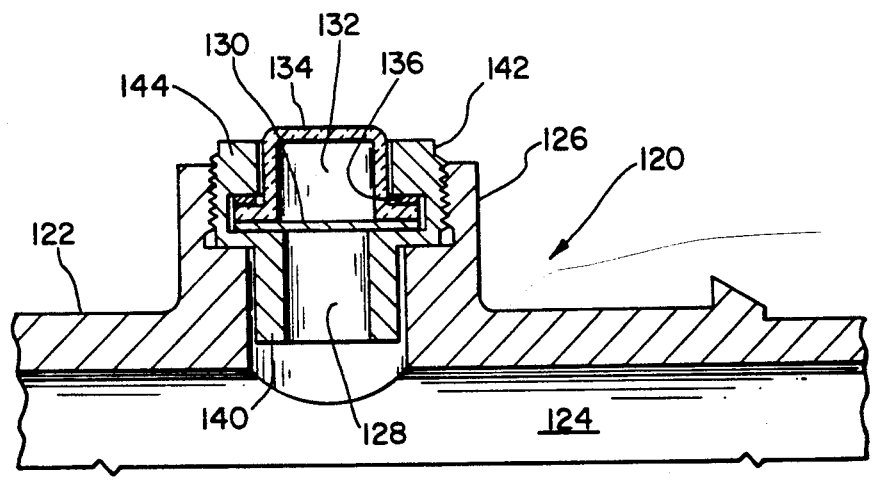
FIG. 9 is an axial cross-section of another embodiment of the invention arranged in a tubular pipe fitting.
Figure 10:
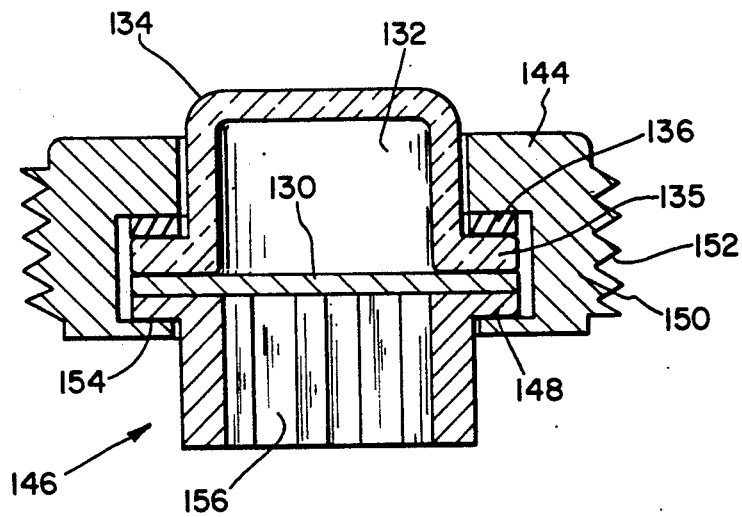
FIG. 10 is a detailed view in cross-section of an embodiment of the invention similar to that shown in FIG. 9, this view omitting the tubular pipe fitting.
Figure 11:
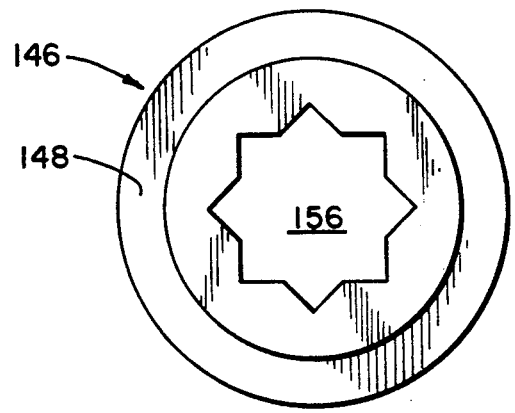
FIG. 11 is an end view of the shaped cathode shown in FIG. 10.

Still another version of the invention is illustrated by FIGS. 9 to 11 wherein the sensor is indicated generally by reference 120. The sensor 120 has a support means in the form of a tubular hose fitting 122 with a fluid passage 124 extending thereto. A cylindrical extension 126 of the fitting projects from one side thereof. An opening 128 in the side of the main passageway permits coolant to flow into the extension where it contacts a metal diaphragm 130. Preferably this diaphragm is selected and constructed so as to corrode and rupture before the heat exchange fluid or coolant becomes so corrosive that it can cause significant damage to the system. A rupture of the diaphragm causes the heat exchanging fluid to flow into a normally empty chamber 132. This chamber is formed on one side by a window element or sight glass means 134. In this version the sight glass is in the form of an inverted cup with an annular flange 135 at the bottom. Located on top of this flange is a suitable seal or rubber gasket 136 which effectively prevents the escape of heat exchanging fluid through the opening 128.

A galvanic couple is formed in the version of FIG. 9 by the corrodible anode partition or diaphragm 130 and a contacting cathode/container 140 which includes a cylindrical bottom extension and a threaded upper portion 142. The cathode/container 140 is made of a noble metal such as copper or possibly titanium. The upper portion threads into the fitting extension 126. The anode partition 130 rests on annular shoulder formed in the cathode/container 140. The cathode/container has an inwardly extending annular lip 144 which engages the top of the seal 136. The cathode/container can be formed around the diaphragm 130 and the flange 135 by known methods such as cold clinching, rolling, or magnaforming. It is also possible to secure the diaphragm to the flange 135 by adhesive, thereby helping to seal the chamber 132. If desired, the rubber gasket 136 can extend around the edge of the flange 135 and the edge of the anode.

The version of the sensor shown in FIG. 10 is similar to that of FIG. 9 except that there is a separate, shaped cathode 146, a bottom end view of which is shown in FIG. 11. The cathode 136 has an outwardly extending flange 148 and the anode 130 rests on top of the cathode. There is a separate, generally cylindrical container 150 which is externally threaded at 152. An annular bottom flange 154 of the container engages the flange of the cathode in order to support same.

The cathode 146 has a shaped passageway 156 extending therethrough. In the illustrated version, the passageway 156 is star-shaped in cross-section, thus presenting a large surface area to the heat exchanging fluid or coolant. The version of FIGS. 10 and 11 has the advantage of providing a relatively large cathode:anode surface area ratio. Because of this a large galvanic driving force is provided and this gives the device the required sensitivity. The preferred material for the more noble metal of the cathode is copper or titanium.

According to the aforementioned published paper entitled "Controlled Release of Inhibitors for Extended Protection of Aluminum in Engine Cooling Systems" by Brian Cheadle et al. a representative aluminum alloy namely AA7072, that is locally thinned and galvanically coupled to the noble metal titanium, will corrode at lower levels of coolant depletion than a representative aluminum alloy used in radiators, namely type 3003. Furthermore cast aluminum corrosion tests in simulated depleted coolants have indicated that relatively high degrees of coolant depletion are required to initiate corrosion damage in aluminum cylinder head material compared to corrodible diaphragm material.

Generally speaking the cathode materials used herein can be any metal or material (i.e. graphite) that is cathodic to the anode provided (that is there should be a large difference in the galvanic series) and that is unlikely to polarize or passivate in service.

Figure 12:
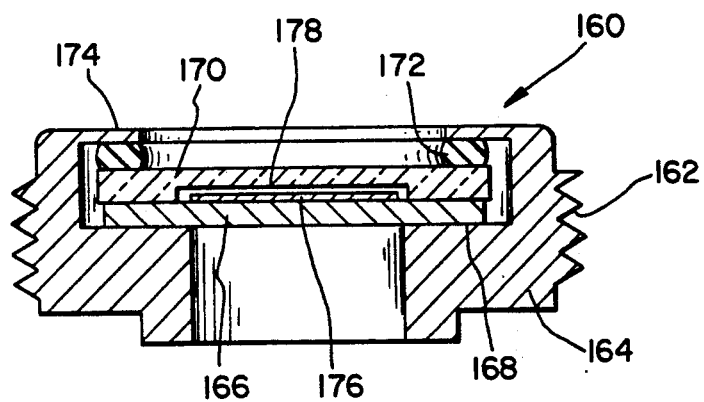
FIG. 12 is a detailed cross-section of a further version of the invention employing a flat anode member and a cathode with external threading for attaching the unit in a pipe fitting.

Another version of the invention which uses a combined cathode/container in which the anode partition is mounted is shown in FIG. 12. It will be understood that this sensing device 160 as illustrated is designed to be threaded into a tubular hose fitting of a type shown in FIG. 9. For this reason, it has external threads 162 provided on a cathode/container 164. An anode partition 166 rests on a shoulder 168 formed by the cathode/container. Located directly on top of the anode 166 is a substantially flat sight glass or window 170. A seal or rubber gasket 172 is arranged around the circumference of the sight glass which is held in place by an upper, inwardly extending flange 174.

Again, if desired, the gasket 172 can be C-shaped in cross-section and can extend around the edge of the sight glass and the edge of the anode.

Sandwiched between the anode 166 and the sight glass 170 is a layer of colour changing dye 176 or a wafer of same. If desired the sight glass 170 can have a shallow recess 178 in a central portion thereof to accommodate this dye material. It will be understood that upon rupture of the anode 166 the liquid coolant will contact the dye material causing it to change colour, for example to the colour red. This will indicate to the user of the vehicle or the mechanic that it is time to change or treat the coolant.

Figure 13:
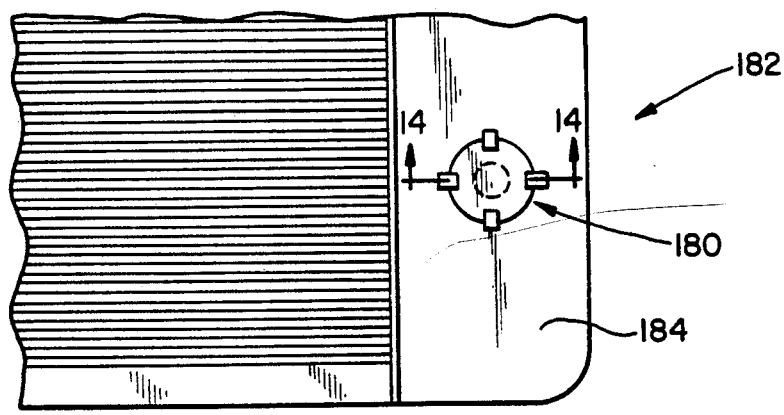
FIG. 13 is a schematic view of a corner of a vehicle radiator showing the location of another version of the invention.
Figure 14:
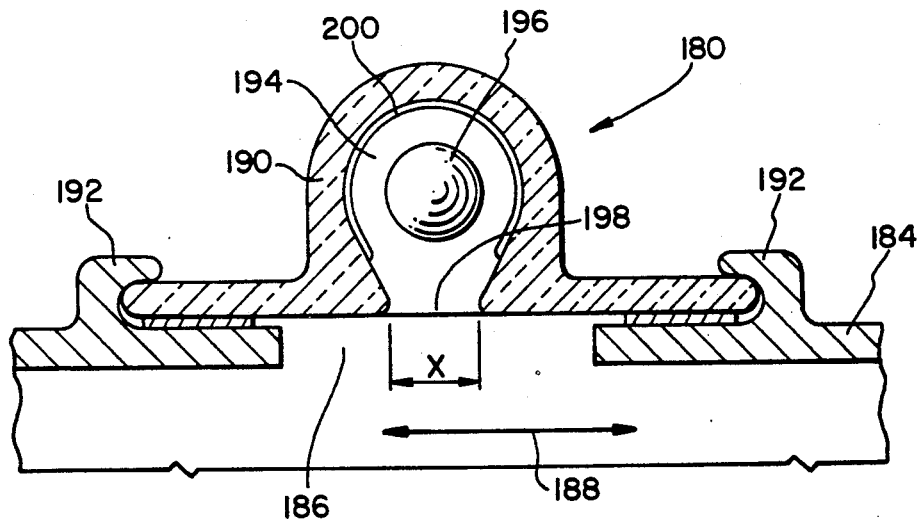
FIG. 14 is a cross-sectional view taken along the line XIV—XIV of FIG. 13.

Still another version of the invention is shown in FIGS. 13 and 14. In this version the sensor 180 is shown installed in the side of a radiator tank 182, only a lower portion of which is shown in FIG. 13. The possible location of this sensor 180 is also shown in dashed lines in FIG. 1 which illustrates a complete radiator. The metal sidewall 184 of the tank is provided with a hole 186 where the sensor is to be located. The coolant or heat exchanging fluid circulates by this hole as indicated by the arrow at 188. In this version the wall of the tank forms part of a support means for mounting the sensor. A sight glass 190 is mounted on the outside of the tank wall by connecting tabs 192. The sight glass in this version comprises a glass dome with a hemispherical top. Formed inside this dome is a fluid chamber 194. Visual indicating means are provided in this fluid chamber and these comprise a single coloured ball 196. The glass dome has a restricted throat 198 having a width X. It will be understood that the diameter of the ball 196 exceeds the distance X so as to provide means for restraining movement of the ball in the sensor. Thus the ball cannot escape from the sensor 180 into the tank 182.

A corrodible opaque coating 200 selected from an anodic material such as aluminum, zinc or magnesium is provided on the inner surface of the sight glass and is located so that heat exchange fluid or coolant contacts the coating during use of the sensor. The coatings may be as pure metals, or as alloys, for instance aluminum and magnesium alloys. The coatings may be deposited by electroless or electrolytic plating, or by vacuum deposition (for example evaporative coating, sputtering, etc.) or chemical deposition methods. As this opaque coating is corroded away by the coolant (when it reaches a corrosive state) the ball 196 will become visible, thereby indicating a need to replace or treat the coolant.

Figure 15:
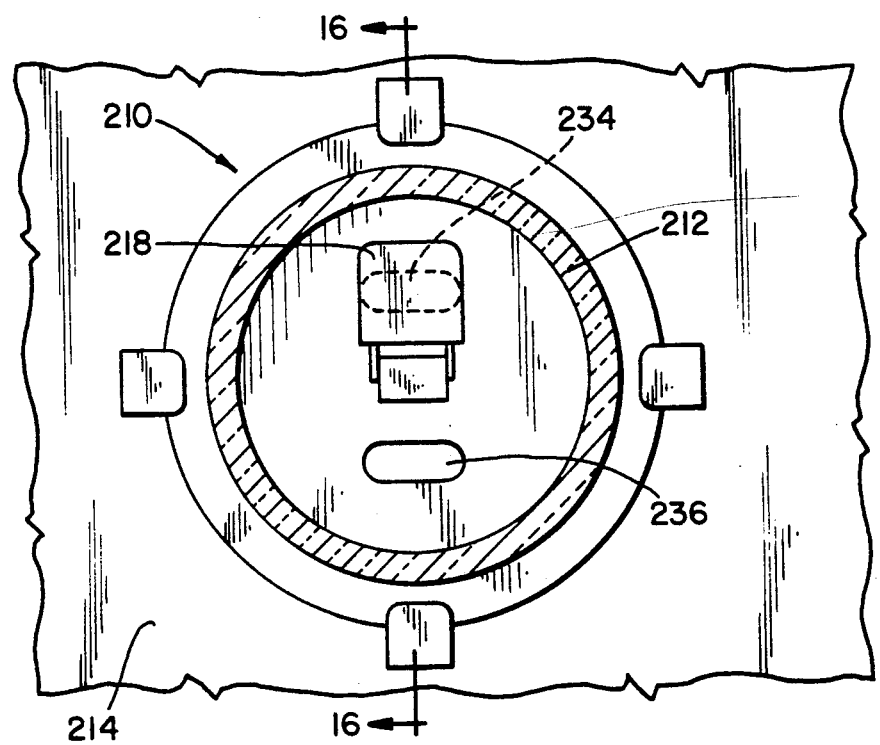
FIG. 15 is a cross-sectional detail similar to that of FIG. 14 but showing still another embodiment of the invention employing a movable indicator.
Figure 16:
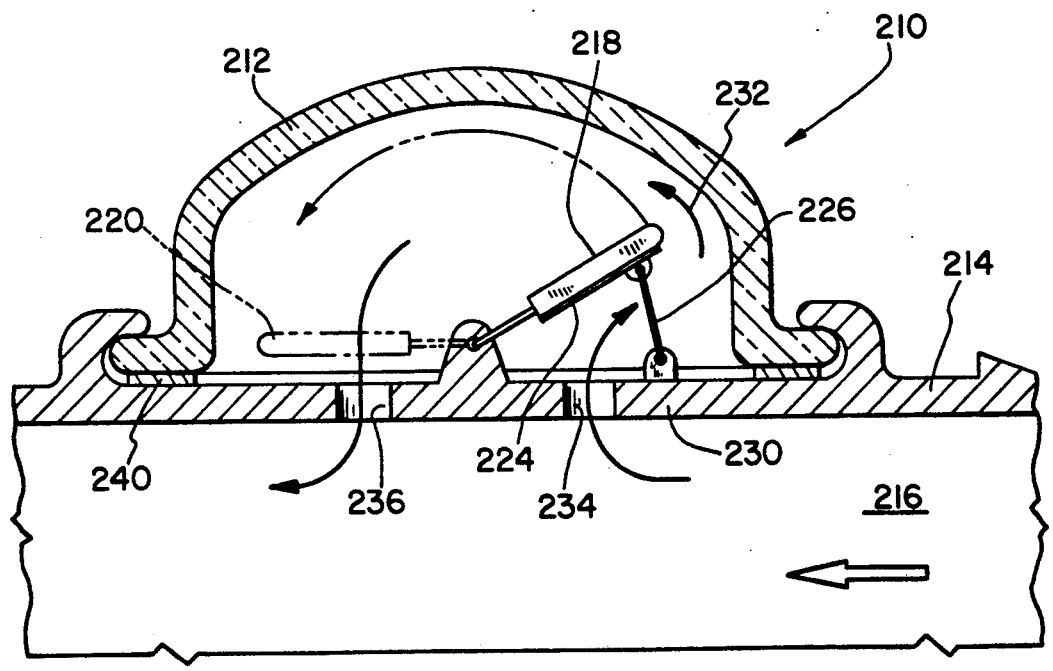
FIG. 16 is a front view of the embodiment of FIG. 15.

Another sensor 210 employing a glass dome 212 is shown in FIGS. 15 and 16. The illustrated support means for mounting the sensor is a wall 214 of a radiator tank. Thus coolant circulates by the sensor 210 as indicated by the arrow 216. A visual indicator 218 is mounted on the side of the tank and is movable from a first position shown in solid lines in FIG. 15 indicating that the heat exchange fluid is in a non-corrosive state to a second position shown in dashed lines (indicated by reference 220) indicating that the fluid has become corrosive to at least a limited degree. In the illustrated embodiment the indicator is a pivotable flap having different colours on opposite sides of the flap. For example, on the visible side 222 of a flap as it is shown in FIG. 15 there can be the colour green while on the opposite side 224 the flap can be read. It will be appreciated that when the flap moves to the position 220, the red colour will be visible. The sensor 210 has a corrodible release mechanism 226 for holding the indicator in the first position and located so as to be immersed in the heat exchange fluid or coolant during use of the sensor. In the illustrated version the release mechanism is preferably a corrodible metal wire or thin strip between approximately 0.010 inch and 0.050 inch in thickness or diameter, one end of which is connected to the flap and the other end of which is connected to the sensor support, in this case the wall of the tank.

The corrodible material is preferably selected from an anodic metal such as aluminum, zinc or magnesium. Testing has been conducted primarily on aluminum, aluminum-zinc alloys, and magnesium alloys. Examples of such alloys are AA7072 aluminum-zinc and MIX or AZ31 magnesium alloys. The corrosion rate of these materials is adjusted by the alloy content, thickness or galvanic coupling. Preferred materials for the wire or strip are AA7072, A231 or MIX magnesium. Wire thicknesses of less than 0.010 inch are feasible but are increasingly subject to metal degradation or handling damage during manufacture as the thickness is reduced. Wire thicknesses from 0.050 inch to about 0.125 inch are also possible and can be made to corrode in relatively short times. However, it becomes more difficult to ensure a penetration or separation of the corrodible material at thicknesses much above 0.10 inch. Instead of a wire or strip configuration, a metal spring connector can be used.

A preferred form of corrosion rate adjustment is the galvanic coupling to a noble metal such as copper and titanium and this can be used in the embodiment of FIGS. 15 and 16. In such a case the wire 226 can form the anode while either the indicator 218 or the material at 230 to which one end of the wire is connected can form the cathode and be made of a cathodic material.

are set out in Table I on the accompanying page. These tests were in the nature of "glassware" corrosion testing (ASTM D1384) measuring time to perforation in corrosive water, depleted coolant and fully inhibited coolants. The magnesium alloy tested was M1X. Aluminum alloys 3003 and 1145 are considered representative of aluminum radiator materials and these also were tested. In these tests these two aluminum alloys were locally thinned to make a "worst case" comparison to candidate corrodible materials. The tests indicate that candidate corrodible materials perforate much faster than radiator materials in the same corrosive environment. Thus these tests indicate that the present sensors employing suitable corrodible materials do have the ability to indicate a corrosive condition in the cooling system prior to damage to the system.

TABLE I

GLASSWARE CORROSION TESTING (ASTM D1384 METHOD, CYCLIC HEATING TO 88° C., 8 HRS. ON/16 HRS. OFF

| | | PERFORATION TIME (DAYS) | | | | |
|---|---|---|---|---|---|---|
| ALLOY | CONDITION | 330 ppm $Cl^-$ + 1 ppm $Cu^+$ Corr. water | ASTM Corr. Water | Tap Water | ¼ Rec. Dose* (12.5%) PII Balance ASTM Corr. Water | 50% PII Balance tap water (Fully Inhibited) |
| | | ← (Increasing Corrosivity) → | | | | |
| Mix Mg (1% Mn, Bal. Mg) | .050" thick galvanically coupled to Cu | — | — | — | 6 | >40 |
| AA 7072 | .010" thick coined to .0016" coupled to Ti | <1 | 1 | 2 | 8 | >120 |
| AA 7072 | .010" thick coined to .0016" no couple | 3 | — | — | — | — |
| AA 2024 | .004" thick no coin no couple | 5 | — | >30 | — | >120 |
| AA 3003 | .010" thick coined to .004" no couple | >19 (Pitting corrosion initiated Day 16) | — | — | — | >120 |
| AA 1145 | .010" thick coined to .004" no couple | >22 | — | — | — | >120 |

*Note:
PII = Prestone II antifreeze. A 50% concentration in tap water is recommended as a fully protected "dose". A 12.5% concentration is thus a "¼ dose"; this low concentration in ASTM corr. water is considered moderately corrosive, and representative of a depleted coolant condition.

The thus formed galvanic couple provides means for controlling the corrosion of the spring.

In this version and in the earlier versions employing a corrodible diaphragm or corrodible coating, a galvanic coupling can be provided by coating or cladding corrodible material with a noble material. In this variation the noble material is locally removed to expose an anodic area for preferential corrosion attack.

Two holes are provided in the side of the tank to permit the circulation of fluid through a chamber 232 formed by the glass dome. These holes 234 and 236 are preferably located on opposite sides of the hinge axis of the indicator 218. When the release mechanism 226 breaks, the heat exchanging fluid flow in the chamber causes the indicator or flap to move to the second position at 220. An annular seal or sealant is provided at 240 to prevent leakage of coolant at this location. If desired a flow diverter 242 can be provided on the inside of the tank wall to encourage or divert the flow of coolant through the chamber 232.

A series of "perforation time" corrosion tests of candidate corrodible diaphragm materials (magnesium and aluminum) have been carried out to assess the operation of the sensors described herein. The results of these tests The tests further indicate that these corrodible materials do not corrode or perforate in a fully inhibited coolant (see the last column in the Table) and therefore a corrosive condition will not be indicated prematurely by the sensors described herein.

The corrosion sensor of FIGS. 15 and 16 can be combined of course with a second fluid condition sensor similar to that used in the version of FIGS. 5 and 6, the second sensor providing an indication of the specific gravity of the fluid and thus solution strength. In such a combination, the flow of fluid out through the passageway 236 can be directed to a tube or channel containing one or more balls visible from the outside. It will be further appreciated that the version of FIGS. 15 and 16 need not necessarily be mounted in a radiator tank wall and this version can also be mounted in a tubular hose fitting, if desired.

Figure 17:
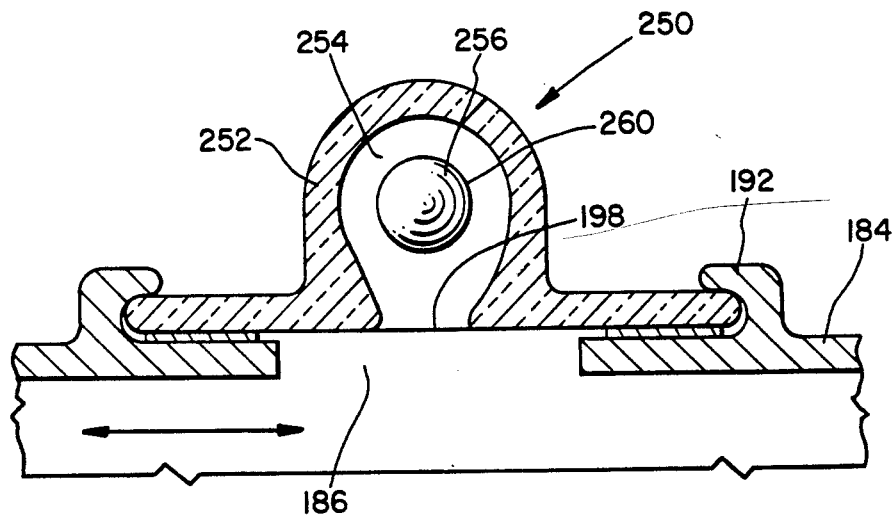
FIG. 17 is a cross-sectional view similar to FIG. 14 but showing a further version of the invention.

FIG. 17 illustrates a further embodiment of the invention which is similar in its appearance to that of FIGS. 13 and 14. However in this version the sensor 250 has a sight glass 252 with no corrodible opaque coating thereon. In other words, the sight glass is clear or transparent at all times. The sight glass is mounted to the side of the tank by means of connecting tabs 192 in the same manner as the version of FIG. 14. Inside the dome of the sight glass is a fluid chamber 254. Again a visual indicator is provided in the fluid chamber in the form of a single coloured ball 256. The ball is restrained from exiting the glass dome by means of restricted throat 198.

In this version the ball 256 has a corrodible coating 260 extending over its entire surface. Because of the circulation of the heat exchanging fluid in the chamber, this fluid contacts the coating during use of the sensor. When the coating is at least partially removed by corrosion caused by the heat exchanging fluid, the ball changes colour as the colour of the coating differs from the colour of the ball on its surface 262.

A preferred version of the ball 256 has an inner or first layer comprising a suitable water soluble material such as water soluble polymer. This inner layer 264 is covered completely with the coating 260 so that the heat exchanging fluid does not initially come into contact with this layer. The purpose of the layer 262 is to provide a "lift-off" of the opaque coating 260 once the initial penetration of the coating has occurred. In this way the entire surface of the ball is quickly cleared of the coating 260 once a corrosive condition in the coolant occurs. Possible water soluble polymers include polyvinyl alcohol, polyoxyethylene or others described in U.S. Pat. No. 4,333,850.

The preferred form of coating for the ball 256 comprises a first layer 266 of anodic corrodible material such as aluminum, zinc or magnesium. These may be pure metals, or alloys. The coating 260 also includes a further or second layer of cathode material at 268 which extends over a substantial portion of the exterior of the anodic material. However, the cathode layer 268 is locally masked or removed at 270 to expose the anodic layer. It will be appreciated that in this way a galvanic couple is provided. The coatings on the ball may be deposited by electroless or electrolytic plating, by vacuum deposition, or chemical vapour deposition methods.

Figure 18:
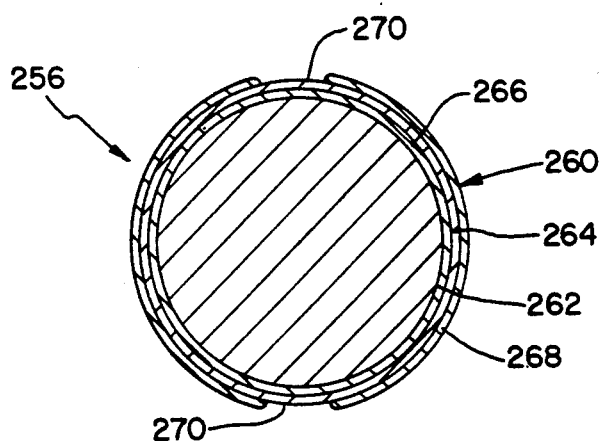
FIG. 18 is a cross-sectional view of the indicator ball used in the embodiment of FIG. 17.
Figure 19:
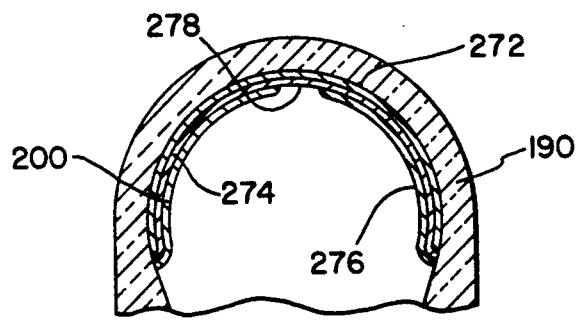
FIG. 19 is a cross-sectional detail of a preferred version of a sight glass usable in the embodiment of FIG. 14.

FIG. 19 is a detailed view illustrating a preferred version of the sight glass used in the embodiment of FIGS. 13 and 14. In this version the sight glass 190 has on the inside of the glass dome an inner layer 272 comprising a suitable water soluble material such as water soluble polymer. The corrodible opaque coating 200 extends over the entire inner layer so as to prevent the heat exchanging fluid from initially contacting the layer 272. As in the ball 256 of FIG. 18, the inner layer 272 is designed to "lift-off" the opaque coating 200 once an initial coating perforation has occurred. In this way the entire inner surface of a sight glass becomes clear quite quickly once a corrosive condition in the coolant occurs. A preferred form of coating 200 includes a first layer of anodic corrodible material 274 and a second layer of cathode material 276 extending over a substantial portion of the exterior of the layer 274. However again the cathode layer is locally masked or removed at 278 to expose the anodic layer. The coating 200 can be deposited in the same manner as the coating on the ball 256.

Figure 20:
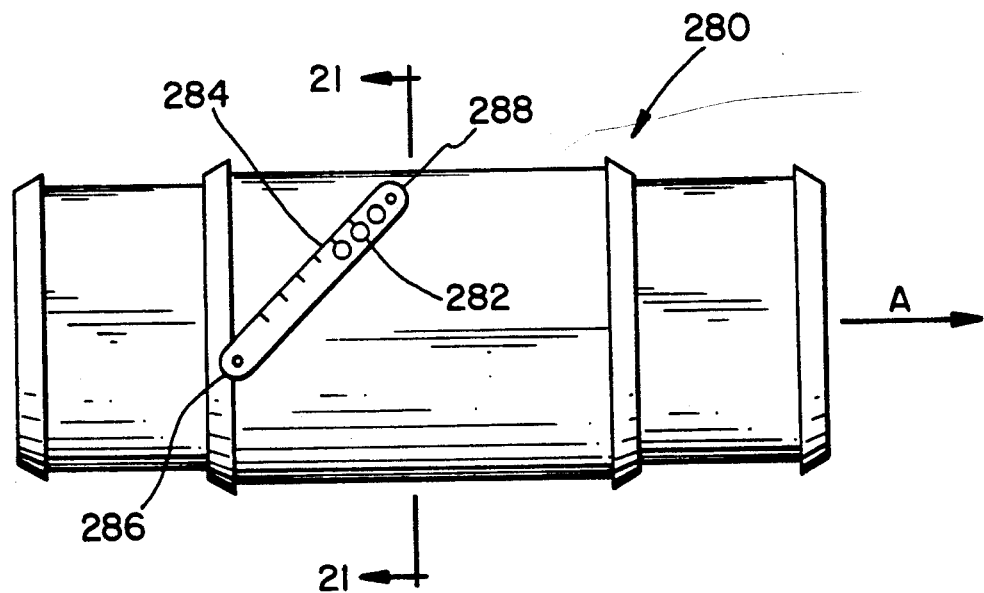
FIG. 20 is a side view of a further embodiment which combines a corrosion sensor with a specific gravity indicator.
Figure 21:
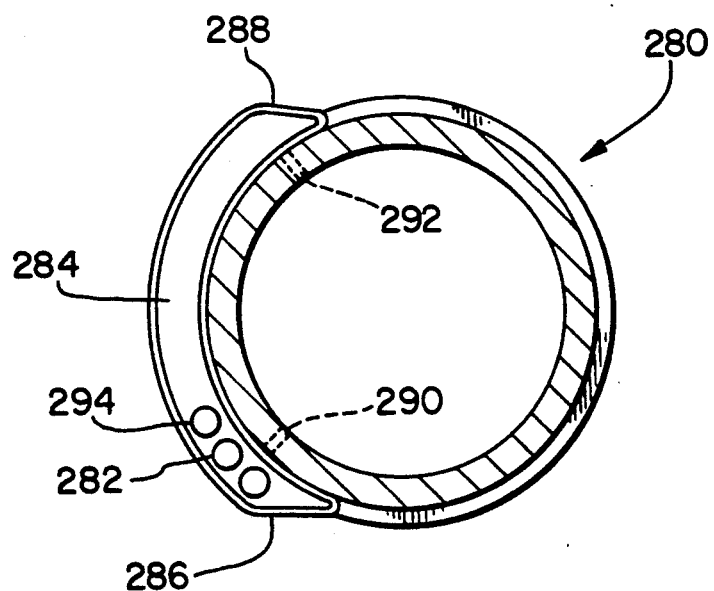
FIG. 21 is a transverse cross-section taken along the line XXI—XXI of FIG. 20.

Turning now to the embodiment illustrated in FIGS. 20 and 21 of the drawings, this embodiment constitutes a combination corrosion sensor and specific gravity indicator indicated generally by 280. As in the embodiment of FIG. 6, this sensor is illustrated in the form of a transparent tubular pipe fitting but in this version there is no corrodible diaphragm. There is a visual indicator which includes one or more coloured balls 282 (three being shown in the drawings) and a transparent tube 284 for holding the ball or balls in heat exchanging fluid contained in the tube. The ball or balls are free to move to a limited extent in the fluid. The tube has a bottom end 286 and an upper end 288. As in the earlier version, the flotation of one or more balls 282 or the lack thereof indicates the specific gravity of the heat exchanging fluid or coolant which in turn indicates the extent to which the fluid provides safe freeze point protection.

In order to permit the circulation of heat exchanging fluid in the tube, two holes 290 and 292 extend between the tube and the interior of the tubular hose fitting. In this embodiment the ball or balls have a corrodible opaque coating 294 thereon, this coating being constructed in the same manner as that on the ball 256 of FIG. 18. Thus the balls are adapted to change their colour when the coating is at least partially removed by corrosion caused by the heat exchanging fluid. It will thus be appreciated that the sensor 280 of FIGS. 20 and 21 provides a dual purpose sensor which is quite simple in its construction.

In those preferred embodiments of the invention employing a metal diaphragm or partition, it is preferable for the metal used to be anodic i.e. aluminum, zinc, or magnesium. It is strongly preferred that the anodic material be coupled to a more noble metal, although the corrosion rate (time) of the corrodible metal can also be adjusted by thinning or forming.

Various methods have been mentioned for securing the diaphragm in place in the fitting. A further method that can be used in the case of a corrodible diaphragm that is coated with the cathodic material is simple injection moulding, the plastic housing being forced around the diaphragm which is secured at the correct location.

It will be clear to those skilled in the construction of radiator and heat exchange systems that various modifications and changes can be made to the described embodiments without departing from the spirit and scope of this invention. Accordingly, all such modifications and changes that fall within the scope of the appended claims are intended to be part of this invention.

What is claimed is:

1. A corrosion sensor for a heat exchange system comprising:

support means for mounting the sensor in said system to enable the sensor to contact heat exchanging fluid flowing through the system;

a transparent viewing member mounted in said support means; and visual indicating means, which can be viewed through said viewing member, having a corrodible opaque coating thereon and located so that said heat exchanging fluid contacts said coating during use of the sensor, wherein said visual indicating means changes its colour when said coating is at least partially removed by corrosion caused by said heat exchanging fluid.

2. A corrosion sensor according to claim 1 wherein said visual indicating means is a coloured movable object, said sensor including means for restraining movement of said movable object in said sensor.

3. A corrosion sensor according to claim 2 wherein said object has an inner layer comprising a water soluble material, said inner layer being covered with said coating.

4. A corrosion sensor according to claim 3 wherein said coating includes a first layer of anodic corrodible material and a second layer of cathode material extending over a substantial portion of the exterior of said first layer but not all of said first layer.

5. A combination corrosion sensor and specific gravity indicator comprising:
- support means for mounting the sensor in said system to enable the sensor to contact heat exchanging fluid flowing through the system;
- a transparent tube mounted in or on said support means;
- means for permitting said heat exchanging fluid to flow into and out of said tube;
- at least one coloured ball located in said tube and held therein so as to be free to move to a limited extent in fluid in said tube, said at least one ball having a corrodible opaque coating thereon and adapted to change its colour when said coating is at least partially removed by corrosion caused by said heat exchanging fluid;
- wherein the flotation of said at least one ball or lack thereof indicates the specific gravity of said heat exchanging fluid and the extent to which said fluid provides safe freeze point protection.

6. The combination device of claim 5 wherein there are several coloured balls located in said tube and held therein and all of said balls have a corrodible opaque coating thereon.

7. The combination device of claim 5 wherein the ball has an inner layer comprising a water soluble material covering its exterior, said inner layer in turn being covered with said coating.

8. The combination device of claim 5 wherein said coating includes a first layer of anodic corrodible material and a second layer of cathode material extending over a substantial portion of the exterior of said first layer but not all of said first layer.

* * * * *